United States Patent
Saito (10) Patent No.: US 7,947,029 B2
(45) Date of Patent: May 24, 2011

(54) UNDERPANTS TYPE DISPOSABLE DIAPER COVER

(75) Inventor: Tetsuhiro Saito, Sakura (JP)

(73) Assignee: Daio Paper Corporation, Ehime (JP)

( * ) Notice: Subject to any disclaimer, the term of this patent is extended or adjusted under 35 U.S.C. 154(b) by 291 days.

(21) Appl. No.: 12/225,786

(22) PCT Filed: Mar. 8, 2007

(86) PCT No.: PCT/JP2007/054502
§ 371 (c)(1),
(2), (4) Date: Sep. 29, 2008

(87) PCT Pub. No.: WO2007/113978
PCT Pub. Date: Oct. 11, 2007

(65) Prior Publication Data
US 2009/0177176 A1    Jul. 9, 2009

(30) Foreign Application Priority Data
Mar. 31, 2006    (JP) .................................. 2006-101154

(51) Int. Cl.
*A61F 13/15*    (2006.01)
(52) U.S. Cl. .......... 604/385.22; 604/385.24; 604/385.25; 604/385.26; 604/385.27; 604/385.29; 604/385.3; 604/396
(58) Field of Classification Search ............. 604/385.22, 604/385.24, 385.25, 385.26, 385.27, 385.29, 604/385.3, 396
See application file for complete search history.

(56) References Cited

U.S. PATENT DOCUMENTS
2005/0131374 A1 *    6/2005    Otsubo et al. ............ 604/385.27

FOREIGN PATENT DOCUMENTS

| JP | 7-299094 | 11/1995 |
|---|---|---|
| JP | 9-99006 | 4/1997 |
| JP | 3058259 | 3/1999 |
| JP | 2001-029375 | 2/2001 |
| JP | 2003-126148 | 5/2003 |
| JP | 2006-14862 | 1/2006 |
| JP | 2006-43415 | 2/2006 |

* cited by examiner

*Primary Examiner* — Jacqueline F. Stephens
(74) *Attorney, Agent, or Firm* — DLA Piper LLP (US)

(57) ABSTRACT

An underpants type disposable diaper cover capable of firmly holding an absorbent pad.

In an underpants type disposable diaper cover comprising a front body part (F) and a back body part (B) which are formed in such a manner as to be continuous with each other at a crotch portion and both side portions, thereby creating a waist opening (23) and a pair of right and left leg openings, and an absorbent pad (10) which is detachably attached to an inner surface thereof, a plurality of waist portion-elastic members (24) are spaced, reaching from one side to the other side, in a longitudinal direction along the waist opening (23) in the front and back body parts (F, B), a plurality of curved elastic members (26, 28) are spaced without intersecting each other in each of the front and back body parts (F, B), which extend from an upper level with respect to a middle level in a longitudinal direction on one side in a lateral direction, to an upper level with respect to a middle level in the longitudinal direction on the other side in the lateral direction, and extend so as to be curved toward the crotch portion with increasing closeness to a central portion in the lateral direction; and a curved portion of at least one of the curved elastic members (28) is configured in the front body part (F) as to pass on both sides with respect to an upper end portion of the attached absorbent pad.

4 Claims, 9 Drawing Sheets

(A) (Developed state)

(B) (Finished product state)

UNDERPANTS TYPE DISPOSABLE DIAPER COVER

FIELD OF THE INVENTION

The present invention relates to underpants type disposable diaper covers to an inner surface of which an absorbent pad is detachably attached, and more particularly to underpants type disposable diaper covers that can reliably hold an absorbent pad to keep the same from slipping down.

TECHNICAL BACKGROUND

Underpants type disposable diaper covers have an absorbent pad detachably attached inside thereof, and are widely used for infants to adults (refer to Patent Documents 1 and 2).

However, conventional diaper covers cannot firmly hold an absorbent pad and thus easily let the same slip down.
Patent Document 1: Japanese Unexamined Patent Publication No. 2001-29375
Patent Document 2: Japanese Utility Model Registration No. 3058259

DISCLOSURE OF THE INVENTION

Problem to be Solved by the Invention

Accordingly, a main object of the present invention is to provide an underpants type disposable diaper cover that can firmly hold an absorbent pad.

Means to Solve the Problem

The present invention to solve the above problem will be described below.
<Invention According to Claim 1>
An underpants type disposable diaper cover, comprising:
a front body part and a back body part which are formed in such a manner as to be continuous with each other at a crotch portion and both side portions, thereby creating a waist opening and a pair of right and left leg openings;
an absorbent pad which is detachably attached to an inner surface thereof;
a plurality of waist portion-elastic members spaced in a longitudinal direction, reaching from one side to the other side along the waist opening in the front and back body parts;
a plurality of curved elastic members spaced without intersecting each other in each of the front and back body parts, which extend from an upper level with respect to a middle level in a longitudinal direction on one side in a lateral direction, to an upper level with respect to a middle level in the longitudinal direction on the other side in the lateral direction, and extend so as to be curved toward the crotch portion with increasing closeness to a central portion in the lateral direction; and
a curved portion of at least one of the curved elastic members configured in the front body part as to pass on both sides with respect to an upper end portion of the attached absorbent pad.
(Operation)
By including the above curved elastic members in the present invention, both sides with respect to the upper end portion of an absorbent pad are stretched in the lateral direction of the ventral side portion and brought upward, whereby the absorbent pad can be firmly held so as not to slip down. Accordingly, it is possible to effectively prevent urine leakage from a ventral side, a leakage mode which is most prone to occur. Incidentally, the above description "front and back body parts . . . continuous with each other at a crotch portion and both side portions" indicates that these body parts include materials which are unseparated and continuous and also materials which are separated but are made continuous by joining separated parts with an adhesive, a heat seal or the like before being processed into products.

<Invention According to Claim 2>
The underpants type disposable diaper cover according to Claim 1, wherein the curved elastic members are arranged in the back body part such that central tip portions of the curved portions therein project in a direction that becomes distant from the crotch portion.
(Operation)
The curved elastic members including projecting portions as described in this claim would be greatly preferable because the projecting portions press an absorbent pad into a cleft between the buttocks to thereby provide an increased fit.

<Invention According to Claim 3>
The underpants type disposable diaper cover according to Claim 1 or 2, wherein start and end points of at least one of the curved elastic members are positioned at the waist opening.
(Operation)
The curved elastic member having start and end points at the waist opening as described in this claim would be preferable because it enhances the power of bringing up an absorbent pad.

<Invention According to Claim 4>
The underpants type disposable diaper cover according to any one of Claims 1 to 3, wherein the waist portion-elastic members are separated from the curved portions of the curved elastic members in each of the front and back body parts, and a plurality of waist elastic members are spaced in the longitudinal direction, reaching from one side to the other side along a waist, so as to pass through at least the separation area.
(Operation)
The curved elastic members may be curved as much as possible toward the crotch portion for enhancement of effectiveness thereof. In this case, however, the waist portion-elastic members are separated from the curved portions of the curved elastic members, which causes a possibility of a decreased fit in the separation area. Accordingly, it is preferable to prevent a decreased fit by filling the entire separation area with the waist elastic members as described in this claim.

(Invention According to Claim 5>
The underpants type disposable diaper cover according to any one of Claims 1 to 4, wherein the curved portion of at least one of the curved elastic members is configured in the front body part as to pass through an edge of the upper end portion of the attached absorbent pad.
(Operation)
The configuration as described in this claim realizes the foregoing operations of the present invention in a more prominent manner.

ADVANTAGES OF THE INVENTION

As stated above, the present invention provides an advantage of firmly holding an absorbent pad, and so on.

DESCRIPTION OF REFERENCE NUMERALS

10 . . . Absorbent pad, 11 . . . Liquid permeable face sheet, 12 . . . Leakage prevention sheet, 13 . . . Absorber, 14 . . . Crepe paper, 15 . . . Gathered nonwoven cloth, 16 . . . Resilient and elastic thread member, 20 . . . Underpants type disposable diaper cover, 21, 22 . . . Side portion-joining edge, 24 . . . Waist portion-elastic member, 25 . . . Waist elastic member, 26 . . . Dorsal side-curved elastic member, 28 . . . Ventral side-curved elastic member, 29 . . . Cutting line around leg, F . . . Front body part, B . . . Back body part

BEST MODES FOR CARRYING OUT THE INVENTION

Embodiments of the present invention will be described in detail with reference to the drawings.

First Embodiment

Figure 1:
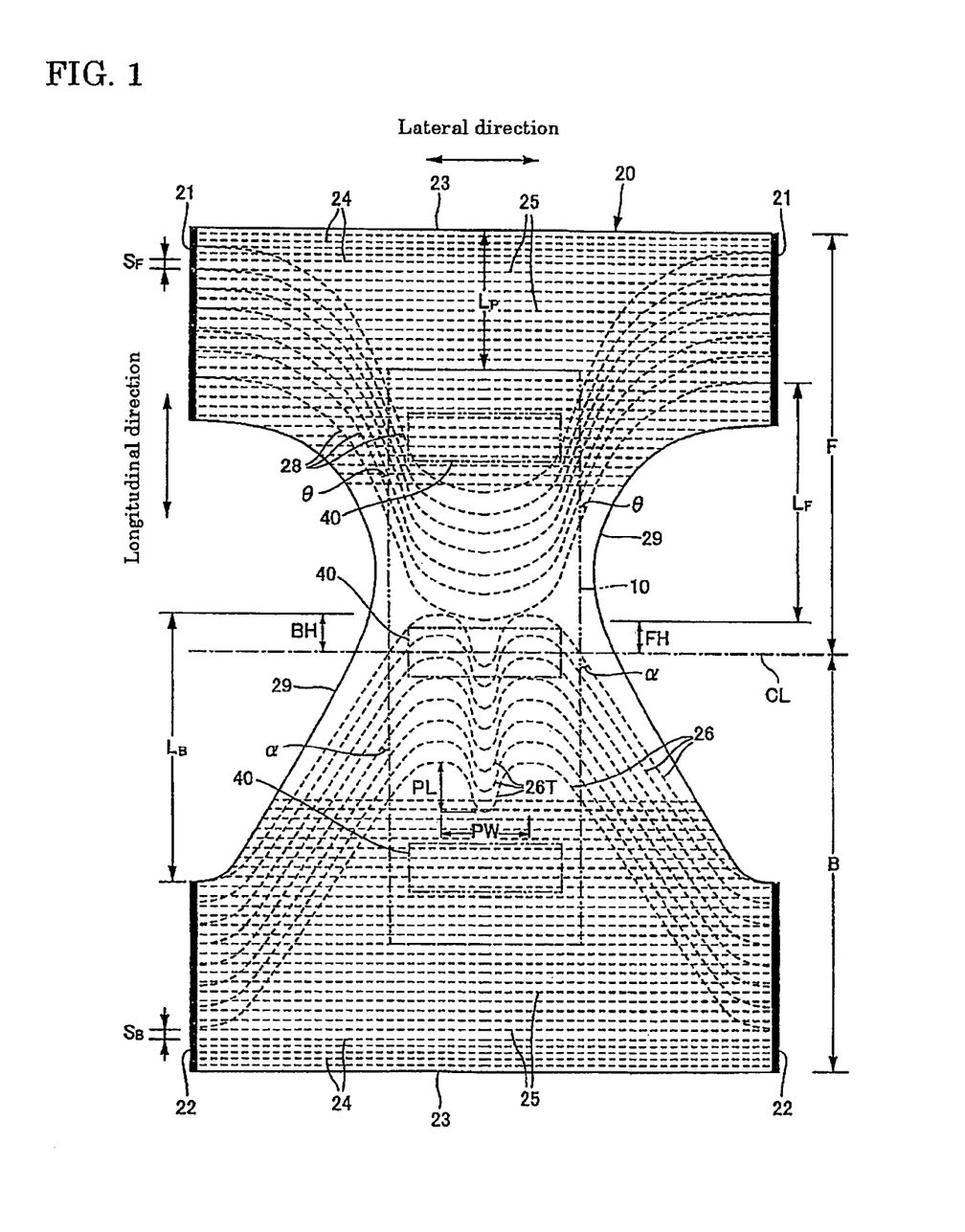
FIG. 1 is a development view of an underpants type disposable diaper cover of a first embodiment.
Figure 2:
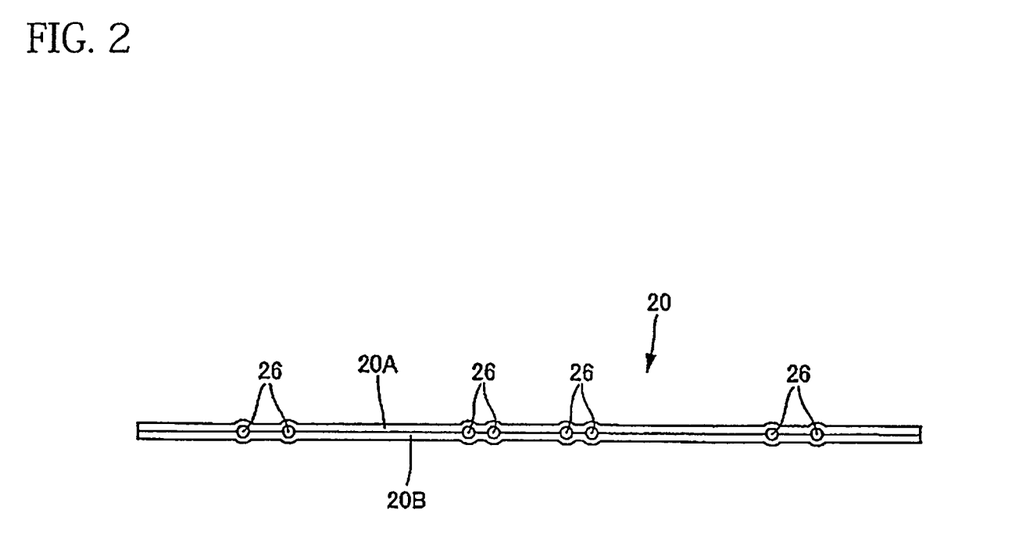
FIG. 2 is a cross-section view of the underpants type disposable diaper cover taken along a folding line.
Figure 3:
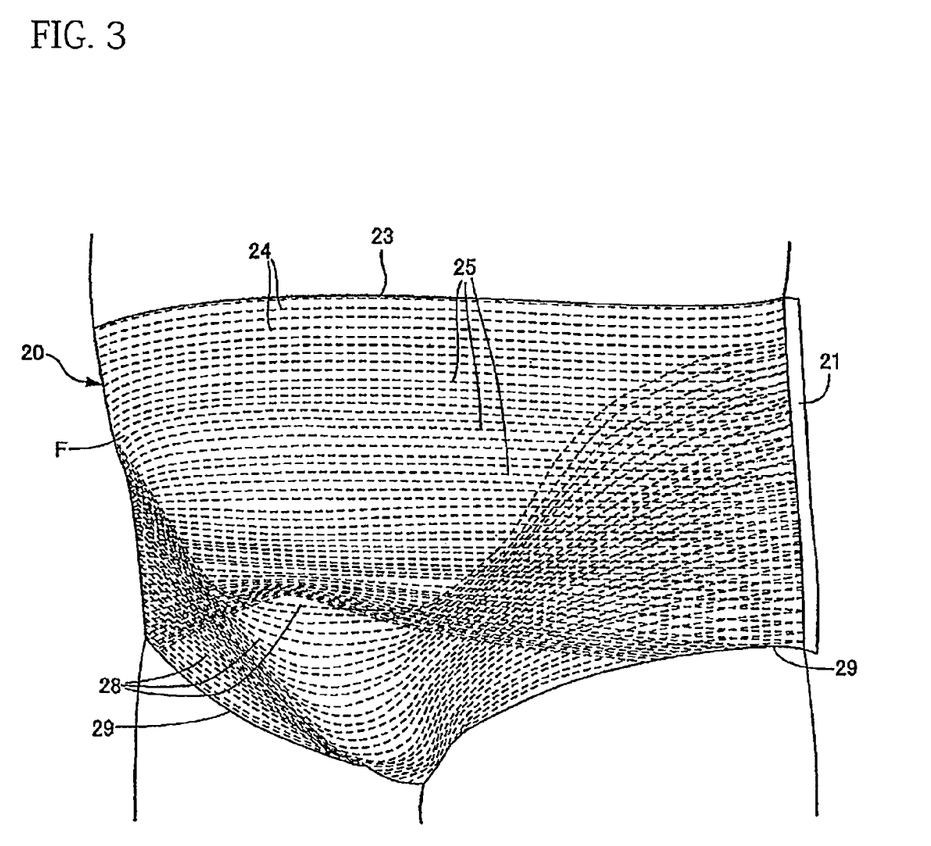
FIG. 3 is an outline view of the first embodiment in an attached state.
Figure 4:
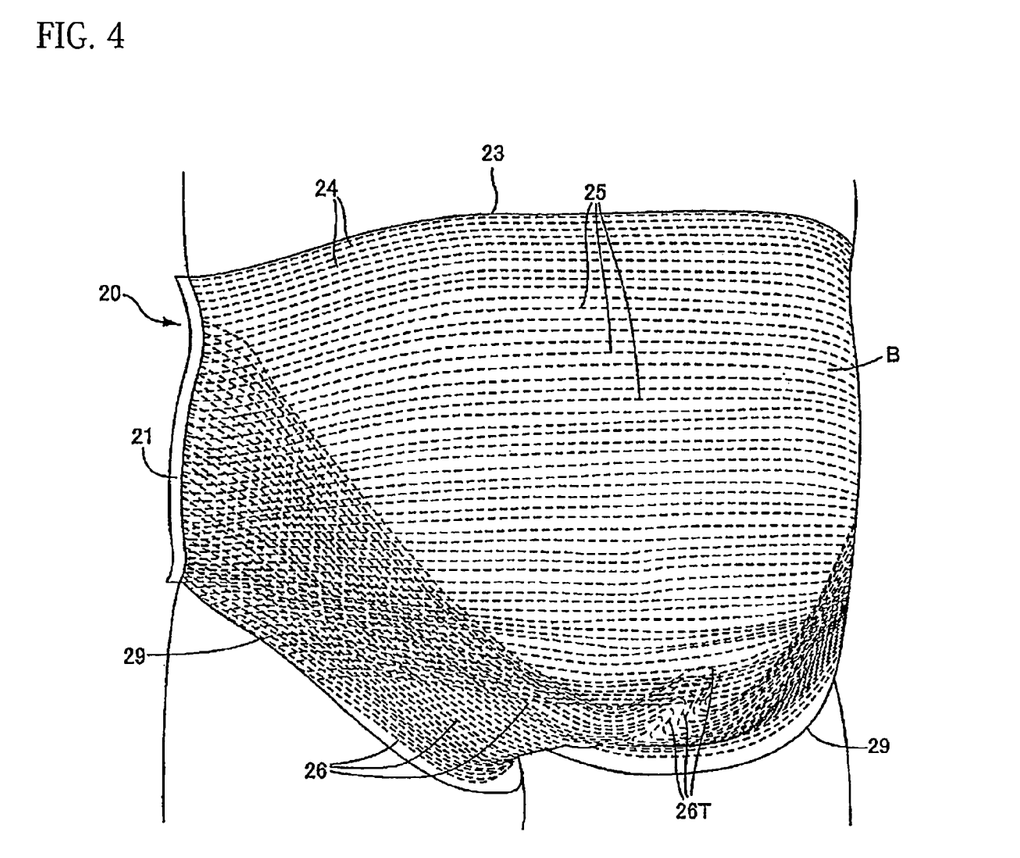
FIG. 4 is an outline view of the first embodiment in an attached state.

An underpants type disposable diaper cover 20 of a first embodiment, as shown in FIGS. 1 and 2, is formed from a two-layer nonwoven cloth sheet including an upper layer 20A and a lower layer 20B, and is provided with stretching properties by various elastic members which are fixed in a stretched state between the upper layer 20A and the lower layer 20B. In a planer figure, a front body part F and a back body part B are integrally formed without being cut off at a crotch portion in a central area in a front-back direction, and a concave cutting line around leg 29 is provided on both sides of the crotch portion, thereby forming a hourglass-like shape as a whole. In this developed state, the front body part F and the back body part B are folded over each other at the crotch portion, and the front body part F and the back body part B are joined together on both sides, which constitutes the underpants type disposable diaper cover 20 having a waist opening and a pair of right and left leg openings as shown in FIGS. 3 and 4.

Usable materials for the diaper cover 20 (in the case of the diaper cover 20 with a multi-layer structure, usable materials for layers thereof) are nonwoven cloths, woven cloths, resin films or the like, regardless of whether porous or nonporous. Those nonwoven cloths are not limited in material fiber and include nonwoven cloths using synthetic fibers such as olefin including polyethylene and polypropylene, polyester, polyamide, and the like, reclaimed fibers such as rayon and cupra, and the like, and natural fibers such as cotton and the like, for example. In addition, those nonwoven cloths are not limited in manufacturing method and include nonwoven cloths manufactured by publicly known processing methods such as a spun lace method, a spun bond method, a thermal bond method, a melt-blown method, a needle punch method and the like, for example. Out of these processing methods, the spun lace method is excellent in flexibility and drape property, and the thermal bond method is superior in volume and softness. In addition, usable resin films include polyolefin resin films such as polyethylene films, polypropylene films, and the like.

As elastic members, a plurality of waist portion-elastic members 24, 24 . . . are spaced in a longitudinal direction (longitudinal direction with respect to a finished product), as shown in FIG. 1, reaching from one side to the other side along a waist opening 23 in the front body part F and back body part B. In addition, a plurality of curved elastic members 26 . . . , 28 . . . are spaced without intersecting one another in each of the front body part F and back body part B, which extend from a portion at an upper level with respect to a middle level in a longitudinal direction on one side in a lateral direction (in the illustrated embodiment, a joining edge on one side at which the front body part F and the back body part B are joined) to a portion at an upper level with respect to a middle level in the longitudinal direction on the other side in the lateral direction (in the illustrated embodiment, a joining edge on the other side at which the front body part F and the back body part B are joined), and extend so as to be curved toward the crotch portion with increasing closeness to a central portion in the lateral direction. Further in the illustrated embodiment, the waist portion-elastic members 24 are separated from the curved portions of the curved elastic members 26 and 28 in each of the front body part F and back body part B. In addition, a plurality of waist elastic members 25, 25 . . . are spaced in the longitudinal direction over a whole longitudinal area containing at least the separation part, reaching from one side to the other side along the waist opening 23. The first embodiment is not provided with elastic members around leg, which are virtually continuous along cutting lines around leg 29.

Suitably used as these elastic members 24, 25, 26 and 28 are thread elastic members formed by generally used styrene-based rubbers, olefin-based rubbers, urethane-based rubbers, ester-base rubbers, polyurethane, polyethylene, polystyrene, styrene-butadiene, silicon, polyester or the like. In addition, elastic tape or film members having a certain width can also be used. Stretchable hot-melt adhesives which elastically extend and contract after solidification can also be used. In particular, thread elastic members and elastic tape members are suitable for the waist portion-elastic members 24 and curved elastic members 26 and 28. Thread elastic members, elastic film members, and stretchable hot-melt adhesives are suitable for the waist elastic members 25, 25 . . . .

Moreover, these elastic members 24, 25, 26 and 28 are favorably 200 to 3,000 dtex or less in thickness, 150 to 350% in tension, and disposed with a spacing of 2 to 20 mm therebetween. In particular, the waist portion-elastic members 24 and the curved elastic members 26 and 28 are favorably 200 to 3,000 dtex or less in thickness, 150 to 300% in tension, and disposed with a spacing of 2 to 10 mm therebetween. In addition, the waist elastic members 25, 25 . . . are favorably 200 to 1,000 dtex or less in thickness, 150 to 280% in tension, and disposed with a spacing of 2 to 20 mm therebetween.

The foregoing elastic members will be sequentially described below in detail.

The waist portion-elastic members 24, 24 . . . are a plurality of rubber thread elastic members spaced in the longitudinal direction in the vicinity of the waist opening edge 23, which are continuous from one side to the other side and provide a stretching force so as to become tight around a waist portion of a wearer. The waist portion-elastic members 24 use rubber thread in the illustrated example, but may use a stretchable tape material instead, for example. A longitudinal area in which the waist portion-elastic members 24 are to be arranged may be decided as appropriate, and may be 1 to 5 cm, for example. The waist portion-elastic members 24 preferably have a stronger tightening force than those of other portions.

Figure 5:
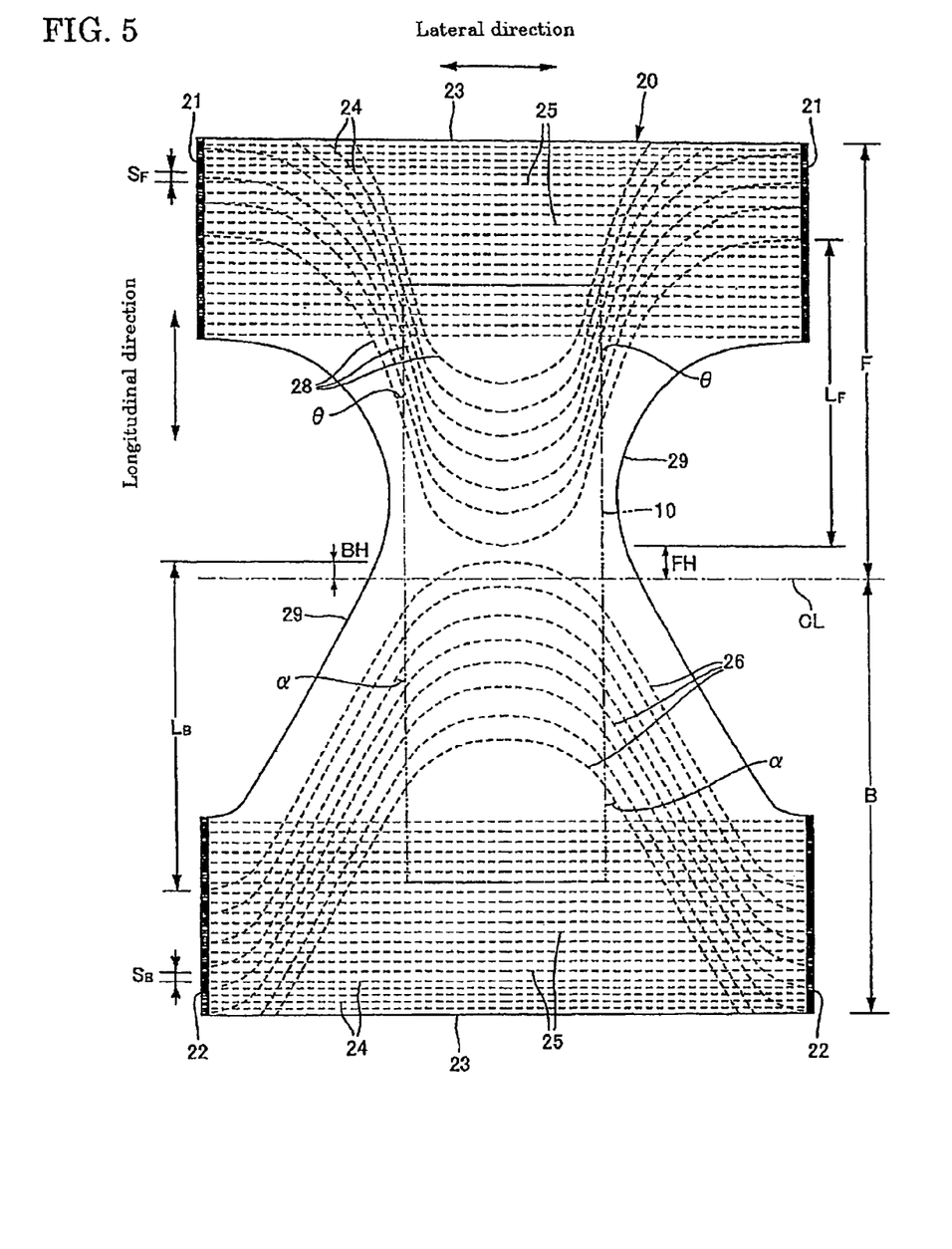
FIG. 5 is a development view of a modified example of the first embodiment.

The waist elastic members 25, 25 . . . are rubber thread elastic members spaced in the longitudinal direction along the waist portion in each of the front body part F and back body part B. If the waist portion-elastic members 24 are separated from the curved portions of the curved elastic members 26 and 28, the waist elastic members 25, 25 . . . support tightening of the separation part. Therefore, if there is no separation part or if there exists a separation part but the separation part is not to be tightened, the waist elastic members 25, 25 . . . may be omitted. The waist elastic members 25, 25 . . . are provided so as to pass through at least an area covering from a lower end of the waist opening 23 to an upper end of the curved elastic members, and in particular, are preferably provided in 50% or more of a longitudinal range of the separation part. In this case, the waist elastic members 25, 25 . . . may be provided in a range covering from portions corresponding to the side portion-joining edges 21 and 22 to the cutting lines around leg 29 as shown in FIG. 1, or may be provided only in an area corresponding to the side portion-joining edges 21 and 22 as shown in FIG. 5.

Separation distances $S_F$ and $S_B$ between the elastic members positioned closest to the waist opening among the waist elastic members 25, 25 . . . and the lowest members among the waist portion-elastic members 24 are preferably 20 mm or less. Boundaries between the waist portion-elastic members 24, 24 . . . and the waist elastic members 25, 25 . . . are not necessarily definite. For example, out of the elastic members horizontally arranged in the front body part F and back body part B with a longitudinal spacing therebetween, some on the upper side may serve as the waist portion-elastic members 24, even though the number thereof cannot be specified, and the remaining may serve as waist elastic members. In addition, some of the waist elastic members 25 may intersect the waist portion-elastic members 24, as in an example shown in FIG. 6 described later.

The curved elastic members 26 and 28 are provided in the front body part F and the back body part B, respectively, and have the function of enhancing the capability of holding an absorbent pad 10. Dorsal side-curved elastic members 26, 26 . . . in the back body part B are a plurality (eight in the example shown in FIG. 1) of rubber thread elastic members which extend continuously from the side portion-joining edge 22 almost along the cutting line around leg 29 on one side, through the crotch portion, to the side portion-joining edge 22 almost along the cutting line 29 on the other side. These dorsal side-curved elastic members 26, 26 . . . are spaced without intersecting one another. The dorsal side-curved elastic members 26, 26 . . . are not arranged virtually in a bundle of about two or three elastic members with a close spacing therebetween, but arranged so as to form a predetermined stretching zone by five or more, preferably seven or more elastic members with a predetermined spacing therebetween.

A longitudinal spacing between the dorsal side-curved elastic members 26, 26 . . . at the side portion-joining edges 21 and 22 is preferably almost identical to a longitudinal spacing between the dorsal side-curved elastic members 26, 26 . . . at the crotch portion. In addition, out of the dorsal side-curved elastic members 26, 26 . . . , the elastic member positioned closest to the crotch portion is preferably arranged in such a manner as to produce a curve geometry with a distance BH of ±50 mm or less, preferably 35 mm or less, from a crotch portion folding line CL in the diaper. By equally spacing the dorsal side-curved elastic members 26, 26 . . . between the side portion-joining edges 22, 22 and the crotch portion, it is possible to fit the entire cover 20 closely to the body of a wearer with an unfocused, equally balanced elastic force. In addition, by arranging the dorsal side-curved elastic members 26, 26 . . . so as to draw curve geometries of large waves passing through an area in the vicinity of the crotch portion, it is possible to fit and hold the cover 20 tightly with respect to the body of a wearer.

Start and end points of the dorsal side-curved elastic members 26, 26 . . . are preferably arranged with a predetermined spacing therebetween in areas covering from almost upper to lower portions of the joining edges between the front body part F and the back body part B. In addition, the curved portions, which are more curved with increasing closeness to the central portion, are preferably configured in such a manner that a smaller angle α formed by intersecting with a side edge of the absorbent pad 10 becomes 35° or more, preferably 40° or more, and more preferably 45° or more. By arranging the dorsal side-curved elastic members 26 in the back body part B at a low inclination angle as described above, a stretching force acts in a direction that follows as much as possible the shape of swollen buttocks, which allows the underpants type disposable diaper cover 20 to fit closely to the body of a wearer so as to wrap around the buttocks. As a result, the absorbent pad 10 is not shrunk at the central portion and is reliably stuck to the body of the wearer, thereby preventing urine leakage more effectively.

In particular, by arranging central tip portions (central portions in the lateral direction) 26T of the curved portions in the dorsal side-curved elastic members 26 so as to locally project in a direction that becomes distant from the crotch portion (toward the waist opening), the projecting portions 26T press the absorbent pad 10 into a cleft between the buttocks as shown in FIG. 4 to thereby very preferably provide an increased fit. A projecting width PW and a projecting length PL can be decided as appropriate, and as an example, the projecting width PW may be about 1 to 5 cm and the projecting length PL may be about 2 to 10 cm. The projecting portions 26T are preferably provided in all the dorsal side-curved elastic members 26, or alternatively may be provided some of the dorsal side-curved elastic members 26, such as some on the crotch portion side or some on the waist opening 23 side.

In addition, the dorsal side-curved elastic members 26, 26 . . . are desirably biased at the crotch portion toward the front body part F with reference to the crotch portion folding line CL in the diaper. By biasing the dorsal side-curved elastic members 26, 26 . . . at the crotch portion toward the front body part F with reference to the crotch portion folding line CL in the diaper, it is possible to eliminate the diaper's slipping down on the buttock side and fit the underpants type disposable diaper cover 20 into the body of the wearer without slack in the diaper cover 20.

In addition, the dorsal side-curved elastic members 26, 26 . . . are preferably arranged in such a manner that a front-back direction separation distance $L_B$ between a portion positioned closest to the crotch portion and the start and end points is 180 mm or more, more particularly 200 to 320 mm. Accordingly, when the wearer holds the sides of the waist portion and pulls up the diaper, the elastic force of the curved elastic members 26, 26 . . . allows the back body part B of the paper diaper to be easily pulled upward, thereby improving easiness to wear.

Meanwhile, the ventral side-curved elastic members 28, 28 . . . provided in the front body part F are a plurality (six in the example shown in FIG. 1) of resilient and elastic thread members spaced without intersecting one another, which extend continuously from the side portion-joining edge 21 on one side, through the crotch portion, to the side portion-joining edge 21 on the other side. These ventral side-curved elastic members 28, 28 ... are spaced without intersecting one another. The ventral side-curved elastic members 28, 28 ... are also not arranged virtually in a bundle of about two or three elastic members with a close spacing therebetween, but arranged so as to form a predetermined stretching zone by five or more, preferably seven or more elastic members with a predetermined spacing therebetween.

A longitudinal spacing between the ventral side-curved elastic members 28, 28 ... at the side-portion joining edges 21 and 22 is almost identical to a longitudinal spacing between the ventral side-curved elastic members 28, 28 . . . at the crotch portion. In addition, out of the ventral side-curved elastic members 28, 28 . . ., the elastic member positioned closest to the crotch portion is arranged in such a manner as to produce a curve geometry with a distance FH of ±50 mm or less, preferably 35 mm or less, from the crotch portion folding line CL in the diaper. By equally spacing the ventral side-curved elastic members 28, 28 . . . between the side portion-joining edges 21, 21 and the crotch portion, it is possible to fit the entire cover 20 closely to the body of a wearer with an unfocused, equally balanced elastic force. In addition, by arranging the ventral side-curved elastic members 28, 28 . . . so as to draw curve geometries of large waves passing outside an area in the vicinity of the crotch portion, it is possible to fit and hold the cover 20 tightly with respect to the body of a wearer.

Start and end points of the ventral side-curved elastic members 28, 28 . . . are preferably arranged with a predetermined spacing therebetween in areas covering from almost upper to lower portions of the side portion-joining edges 21, 21 between the front body part F and the back body part B. In addition, the curved portions, which are more curved with increasing closeness to the central portion, are preferably configured in such a manner that a smaller angle θ formed by intersecting with a side edge of the absorbent pad 10 becomes 30° or less, preferably 28° or less. The intersection angle θ is desirably at least 20° or more, from the aspect of a balance between a horizontal component force and a vertical component force. Diapers are prone to slip down in the front part of a body due to the absence of a swollen portion like buttocks in the back part. However, by arranging the ventral side-curved elastic portions 28 at a sharp inclination angle, it is possible to effectively prevent the diaper from slipping down and firmly hold the absorbent pad 10.

As a feature of the present invention, at least one, preferably a plurality of ventral side elastic members 28, 28 . . . are arranged in such a manner that the curved portions thereof pass through both sides with respect to the upper end portion of the attached absorbent pad 10. With such a configuration, the both sides of the upper end portion of the absorbent pad 10 are stretched in the lateral direction and brought upward as shown in FIG. 3, whereby it is possible to firmly hold the absorbent pad 10 with respect to the body of a wearer without slipping down.

From the above aspects (that is, the intersection angle of the curved portions and the passage of the curved portions through the both sides of the upper end portion of the absorbent pad 10), as shown in FIG. 5, at least one, preferably a plurality of ventral side-curved elastic portions 28 may be arranged in such a manner that the start and end points thereof are positioned at the waist opening portion 23, as one preferable embodiment.

In addition, the ventral side-curved elastic members 28, 28 . . . are preferably arranged in such a manner that a front-back direction separation distance $L_F$ between a portion positioned closest to the crotch portion and the start and end points is 120 mm or more, more particularly 140 to 250 mm. When a wearer holds the sides of the waist portion and pulls up the diaper, the elastic force of the ventral side-curved elastic members 28, 28 . . . allows the front body part F of the paper diaper to be easily pulled upward, thereby improving easiness to wear.

Incidentally, some of the ventral side-curved elastic members 28, 28 . . . may intersect some of the dorsal side-curved elastic members 26, 26 . . . As in the illustrated embodiment, one of the ventral side-curved elastic members 28, 28 closest to the crotch portion, is desirably adjacent to one out of the dorsal side-curved elastic portions 26, 26 closest to the crotch portion, without intersecting one another at the crotch portion, and an adjacent width (FH-BH) is desirably set to be 10 to 20 mm. At the crotch portion, the curved elastic members 28 . . . , 26 . . . press and fit the absorbent pad 10 closely to the body of a wearer with an equal pressure, which closes a clearance between the pad 10 and the body and prevents leakage in a highly effective manner.

Second and Third Embodiments

Figure 6:
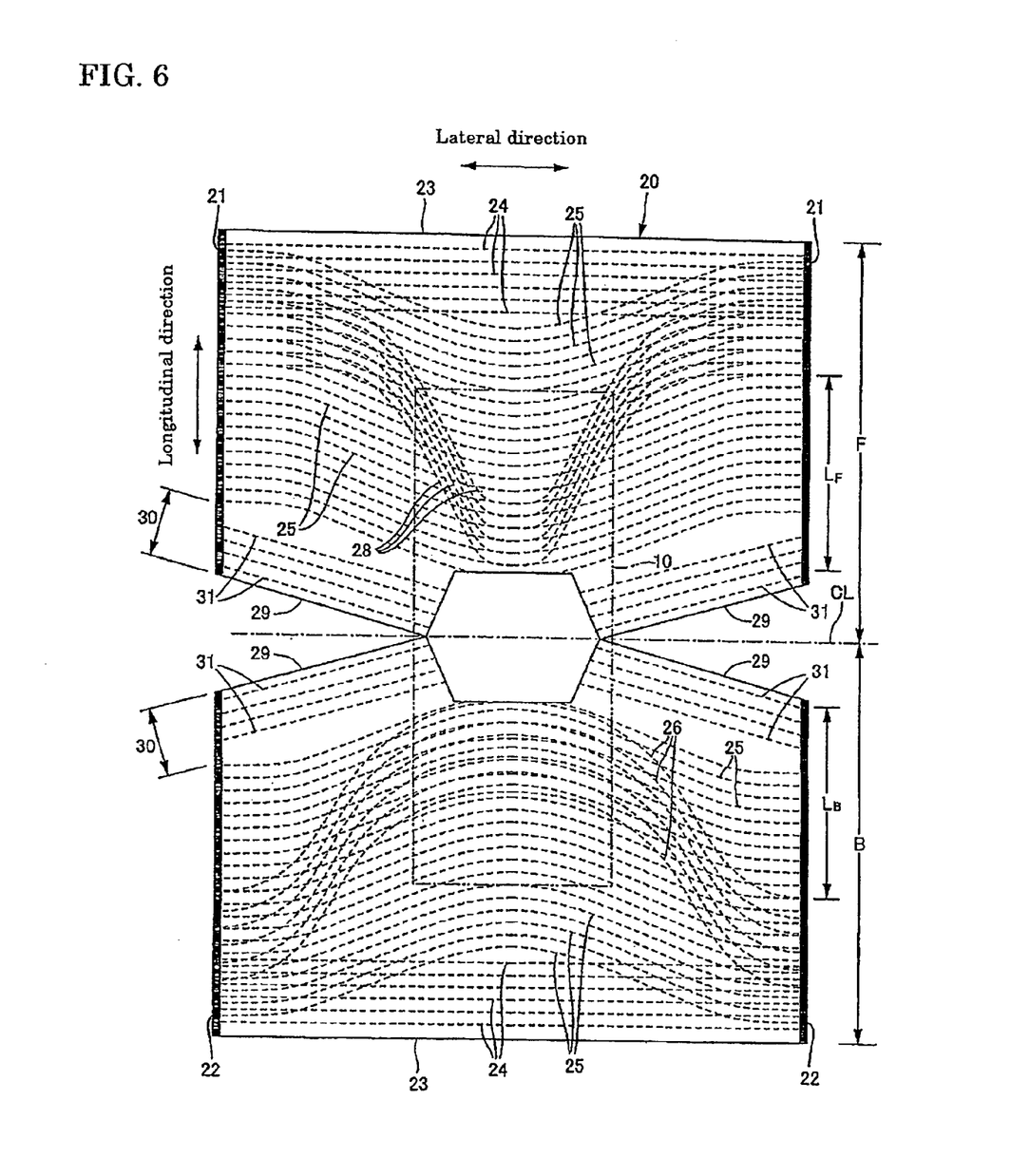
FIG. 6 is a development view of an underpants type disposable diaper cover of a second embodiment.
Figure 7:
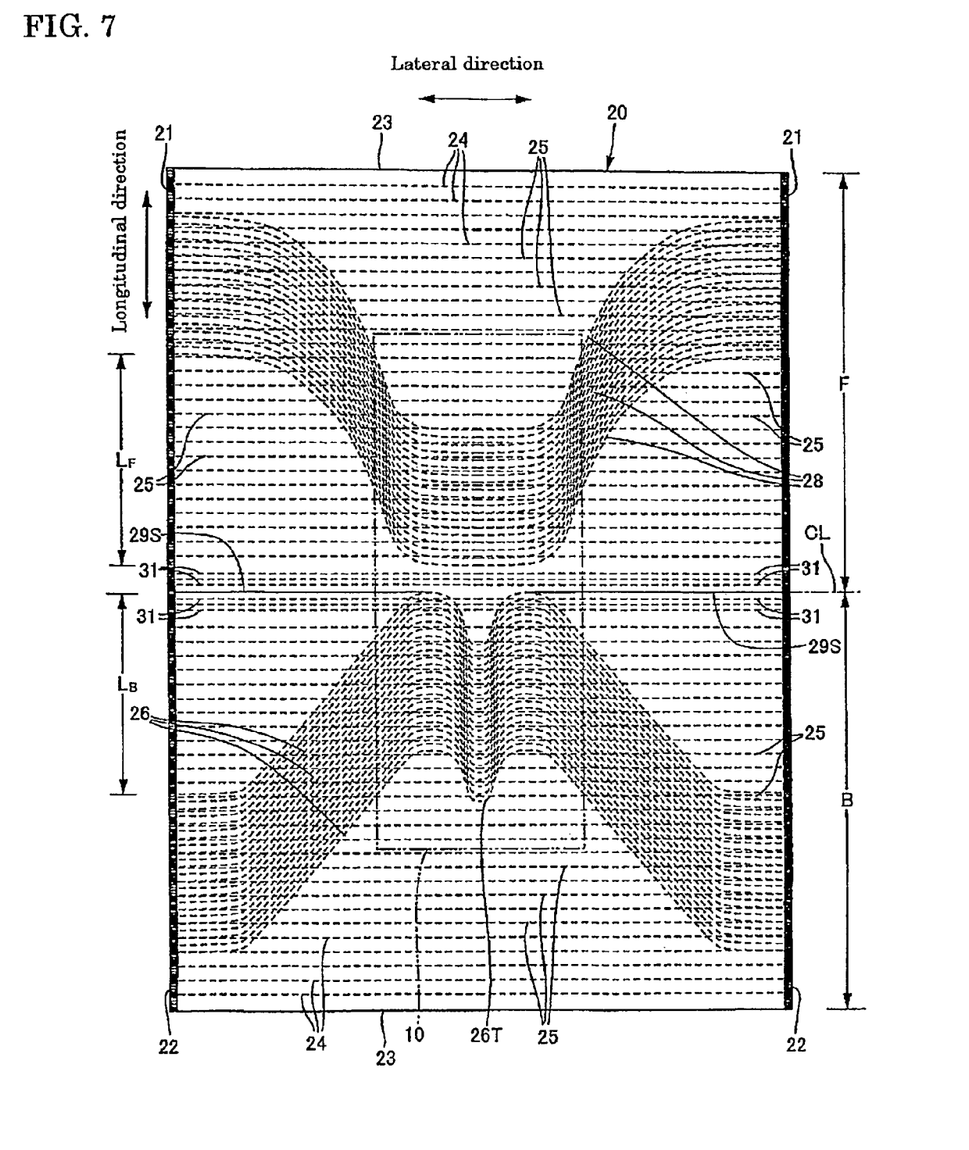
FIG. 7 is a development view of an underpants type disposable diaper cover of a third embodiment.

FIGS. 6 and 7 illustrate applications of the present invention to boxer underpants type diaper covers. In a second embodiment shown in FIG. 6, leg portions 30 surrounding groins are provided, and the front body part F and the back body part B are separated at the crotch portion but are made continuous at end portions on the inner sides (the crotch portion sides) of the leg portions 30. Joining the front body part F and the back body part B at the crotch portion, the leg portions 30 and the both side portions 21 and 22, constitutes a boxer underpants type diaper cover with the waist opening 23 and a pair of right and left leg openings. The waist elastic members 25 are slightly curved toward the crotch portion, and the dorsal side-curved elastic members 26 have no projections shown in FIG. 1. In addition, as compared with the foregoing embodiment, the ventral side-curved elastic members 28 are curved at a sharper angle (in an almost V formation), and the dorsal side-curved elastic members 26 are curved more gently. Further, the leg portions 30 have elastic members 31 around leg along leg portions.

Meanwhile, in an embodiment shown in FIG. 7, each of the cutting lines around leg 29 has no concave shape but is formed by a slit 29S parallel to the waist opening 23, and the front body part F and the back body part B are not separated but made continuous at the crotch portion. Folding the front body part F and the back body part B at the crotch portion as a boundary between the two parts and joining on both sides, constitute a boxer underpants type diaper cover with a waist opening and a pair of right and left leg openings. The waist portion-elastic members 24 and the waist elastic members 25 are arranged over the virtually entire front body part F and back body part B. The curved elastic members 26 and 28 are arranged with a smaller spacing therebetween. In addition, the elastic members around leg 31 are provided along leg portions.

<Example of an Absorbent Pad>

Figure 8:
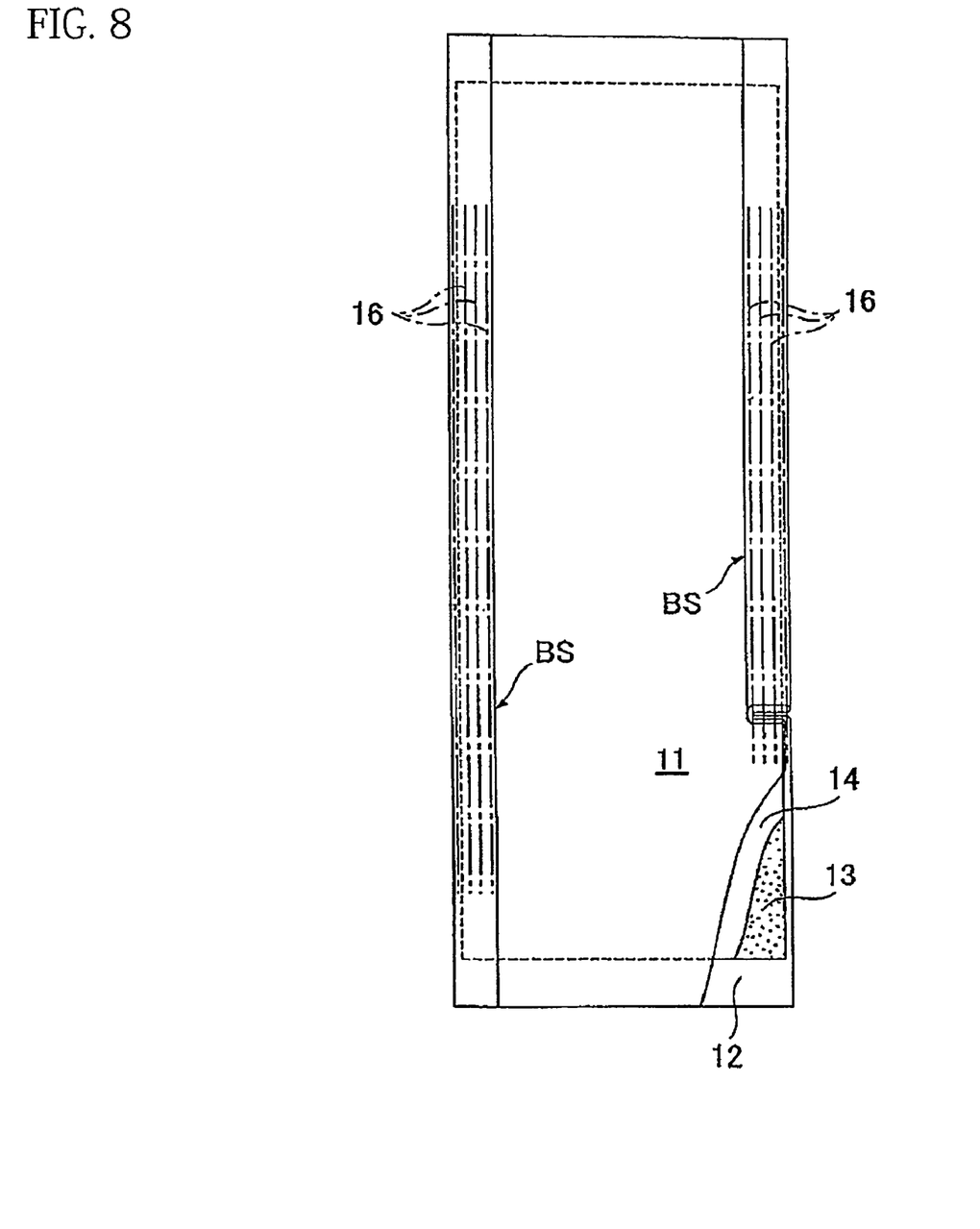
FIG. 8 is a plane view of an absorbent pad.
Figure 9:
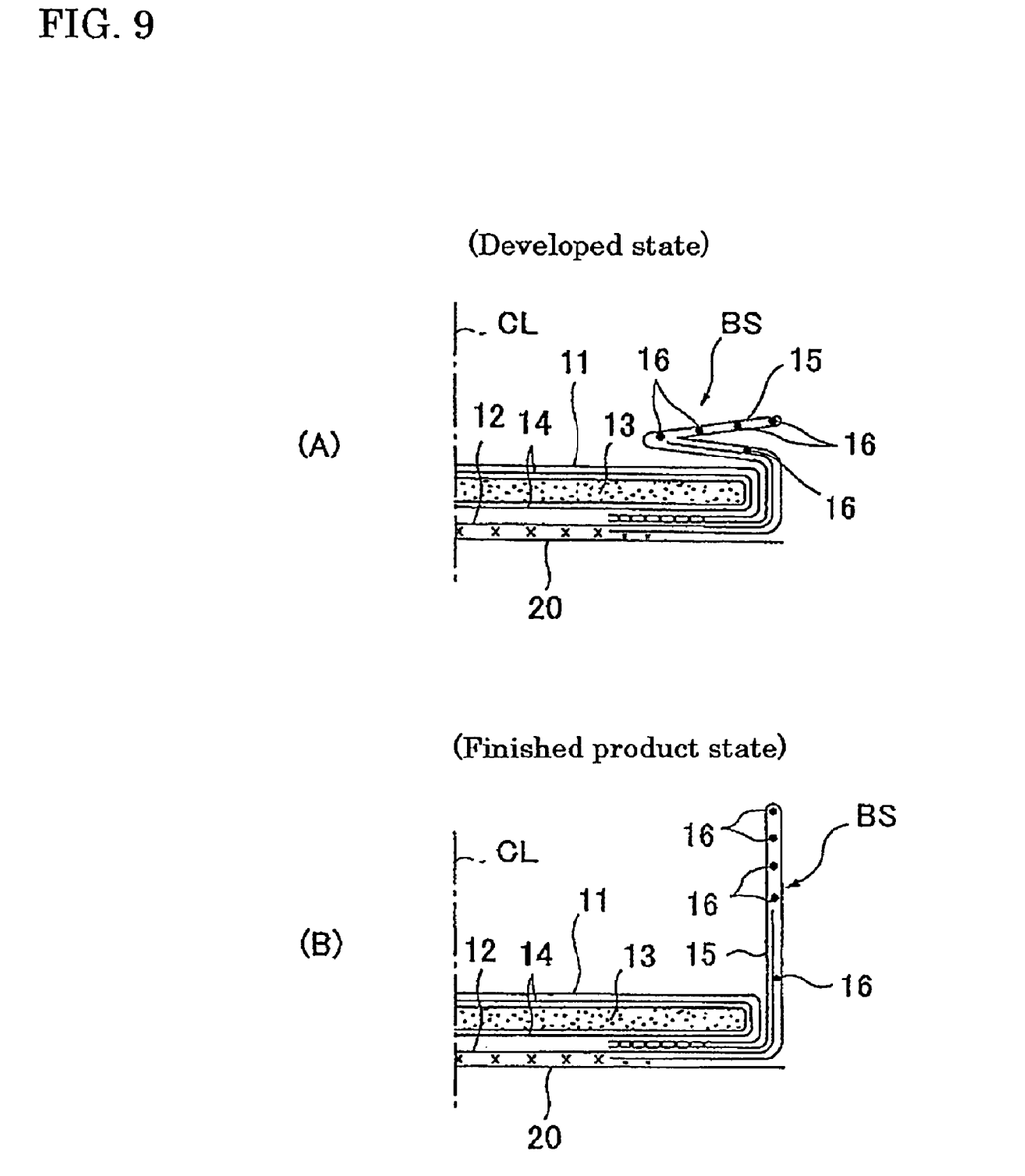
FIG. 9(A) is a semi-cross-section view of the absorbent pad in a developed state.
FIG. 9(B) is a view showing the absorbent pad in a state of a finished product.

The absorbent pad 10 has no limitations as far as the same is detachably attached to the inner surface of a diaper cover. For example, as shown in FIGS. 8 and 9, the absorbent pad 10 is configured as to have a liquid permeable face sheet 11 formed of a nonwoven cloth or the like, a leakage prevention sheet 12 formed of polyethylene or the like, and an absorber 13 formed of a flocculent pulp or the like between the sheets 11 and 12, to thereby absorb and retain a body fluid. The absorbent pad 10 may be simply placed on the inner surface of the cover 20, and preferably is fixed via a fixing means in a removable manner. Incidentally, the mark "*" in FIG. 9 indicates an adhesive layer as the fixing means.

The fixing means has no limitations, and can use an adhesive agent, a mechanical fastener for fixing a target to be fixed by engaging a hook member on one side of the target with a loop member on the other side of the target, a magnetic attaching means for fixing a target to be fixed by attaching magnetically a magnet on one side of the target to a magnet or magnetic metal on the other side of the target, or the like. For the magnet, a rubber magnet can be suitably used.

A position of the fixing means can be decided as appropriate. If the fixing means is an adhesive agent, the adhesive agent may be provided on an outer surface of the absorbent pad 10 (an outer surface of the leakage prevention sheet 12) or on the inner surface of the diaper cover 20. In addition, if the fixing means is a mechanical fastener, a hook member is provided on either the outer surface of the absorbent pad 10 or the inner surface of the diaper cover, and a loop member is provided on the other thereof. Further if the fixing means is a magnetic attaching means, a magnet is provided on either the outer surface of the absorbent pad 10 or the inner surface of the diaper cover, and a magnet or a magnetic metal member is provided on the other thereof.

Although the fixing means has no limitations in shape, size or number, the fixing means is preferably provided so as not to let the absorbent pad 10 slip down while the diaper cover is worn. For example, as shown in FIG. 1, the fixing means 40 may be provided at front and back ends of the absorbent pad 10 and at a central portion in a front-back direction of the same. The power of the fixing means is preferably adjusted in a balanced manner so as to be strong to an extent that the absorbent pad 10 does not slip down and be weak to an extent that the cover 20 is not broken when the attached absorbent pad 10 is removed.

Dimensions of the absorbent pad 10 and an attachment position thereof with respect to the diaper cover 20 can be decided as appropriate. For example, a width of the upper end portion of the absorbent pad 10 may be 100 to 340 mm. In addition, the absorbent pad 10 may be attached such that a vertical separation distance $L_P$ from the waist opening 23 in the diaper cover to the edge of the upper end portion of the absorbent pad 10 is 80 to 220 mm.

In the illustrated example, the absorber 13 is formed in a planar, almost square shape, and has a width with which a wearer does not have a stiff feeling when the absorber 13 comes into contact with a crotch of a wearer. The absorber 13 is enclosed with crepe paper 14 to retain the shape thereof and improve diffusibility of body fluid having passed through the liquid permeable face sheet 11. Desirably used as the absorber 13 is an airlaid absorber that can be reduced in volume.

Suitably used as the liquid permeable face sheet 11 covering a front side (a skin-contact side) of the absorber 13, are porous or nonporous nonwoven cloths, multi-porous plastic sheets and the like. Material fibers for constituting the nonwoven cloths include synthetic fibers such as olefin including polyethylene and polypropylene, polyester, and polyamide, reclaimed fibers such as rayon and cupra, and natural fibers such as cotton, for example. In addition, the usable nonwoven cloths may be obtained by appropriate processing methods such as a spun lace method, a spun bond method, a thermal bond method, a melt-blown method, and a needle punch method, for example. Out of these processing methods, the spun lace method is excellent in flexibility and drape property, and the thermal bond method is superior in volume and softness. The liquid permeable face sheet 11 with a large number of permeable pores absorbs quickly urine or the like and thus is excellent in providing a dry touch. The liquid permeable face sheet 11 involves edges of side portions of the absorber 13 and extends to a back side of the absorber 13.

Used as the leakage prevention sheet 12 covering the back side (the non-skin-contact side) of the absorber 13, is a liquid impermeable plastic sheet formed of polyethylene or polypropylene. In recent years, a moisture-permeable sheet has also been suitably used for prevention of stuffiness. The water-shielding and moisture-permeable sheet is, for example, a microporous sheet obtained by melting and kneading an inorganic filling agent into an olefin resin such as polyethylene or polypropylene to form a sheet and stretching the sheet in a uniaxial or biaxial direction. If the microporous sheet is the same in thickness as a nonporous sheet, the microporous sheet is lower in stiffness than the nonporous sheet and therefore is superior in flexibility to the nonporous sheet.

Meanwhile, as shown in FIG. 9, a gather nonwoven cloth 15 with three dimensional gathers BS, which is folded back so as to be a duplicate sheet, involves the edges of side portions of the absorber 13 involved by the liquid permeable face sheet 11, from a further upper level with respect thereto, and extends and attaches to the back side of the absorber 13. More specifically, the gather nonwoven cloth 15 is adhered by a hot-melt adhesive agent or the like to the central portion in the longitudinal direction of the paper diaper in an area covering from the central portion in the lateral direction to the back side of the absorber 13, except for three dimensional gather BS-forming portions. In addition, the gather nonwoven cloth 15 is adhered to the front and back ends in the longitudinal direction in an area covering from a section from the central portion in the lateral direction to an edge of one side, to the back side of the absorber 13. Further, the gather nonwoven cloth 15 is folded and adhered by a hot-melt adhesive agent or the like at the three dimensional gather BS-forming portions on the upper surface of the absorber 13.

A plurality of resilient and elastic thread members 16, 16 . . . are disposed at standing edge side portions in an interior of the gather nonwoven cloth 15 formed of a duplicate sheet nonwoven cloth. As shown in FIG. 9(B), the resilient and elastic thread members 16, 16 . . . are intended in a state of a finished product to form three dimensional gathers BS by letting stand nonwoven portions projecting from the edges of side portions of the absorber with an elastic stretching power.

The leakage prevention sheet 12 enters the interior of the duplicate-sheet gathered nonwoven cloth 15 to constitute a leakage prevention wall at a lower end of the three dimensional gathers BS as shown in FIG. 9. The leakage prevention sheet 12 is desirably opaque so as not to show dark colors of defecation, urine and the like. Suitably used for the opaque sheet is a film which is formed from a plastic material mixed with pigments and filling agents such as calcium carbonate, titanium oxide, zinc oxide, white carbon, clay, talc, and barium sulfate.

Usable materials for the resilient and elastic thread members 16 are commonly-used styrene-based rubbers, olefin-based rubbers, urethane-based rubbers, ester-based rubbers, polyurethane, polyethylene, polystyrene, styrene-butadiene, silicon, polyester, and the like. In addition, to decrease visibility from outside, the resilient and elastic thread members 16 are favorably 925 dtex or less in thickness, 150 to 350% in tension, and arranged at a spacing of 7.0 mm or less therebetween. Instead of the resilient and elastic thread members, resilient and elastic tape members having a certain width may be used.

Similarly to the liquid permeable face sheet 11, material fibers for constituting the gather nonwoven cloth 15 include synthetic fibers such as olefin including polyethylene and polypropylene, polyester, and polyamide, reclaimed fibers such as rayon and cupra, and natural fibers such as cotton. The usable nonwoven cloths may be obtained by appropriate processing methods such as a spun bond method, a thermal bond method, a melt-blown method, and a needle punch method. In particular, it is preferred to use a nonwoven cloth with a reduced basis weight and excellent in air permeability for prevention of stuffiness. Further, desirably used as the gather nonwoven cloth 15 is a water-repellent nonwoven cloth coated with a silicon-, paraffin metal-, or alkyl chromic chloride-based water repellent agent to thereby prevent permeability of urine or the like and skin rash and to improve a skin feel (dry touch).

INDUSTRIAL APPLICABILITY

The present invention is applicable to an underpants type disposable diaper covers in which an absorbent pad can be detachably attached to the inner surface thereof.

The invention claimed is:

1. An underpants type disposable diaper cover, comprising:
   a front body part and a back body part which are formed in such a manner as to be continuous with each other at a crotch portion and both side portions, thereby creating a waist opening and a pair of right and left leg openings;
   an absorbent pad which is detachably attached to an inner surface thereof;
   a plurality of waist portion-elastic members spaced in a longitudinal direction, reaching from one side to the other side along the waist opening in the front and back body parts;
   a plurality of curved elastic members spaced without intersecting each other in each of the front and back body parts, which extend from an upper level with respect to a middle level in a longitudinal direction on one side in a lateral direction, to an upper level with respect to a middle level in the longitudinal direction on the other side in the lateral direction, and extend so as to be curved toward the crotch portion with increasing closeness to a central portion in the lateral direction; and
   a curved portion of at least one of the curved elastic members configured in the front body part as to pass on both sides with respect to an upper end portion of the attached absorbent pad; and
   wherein the curved elastic members are arranged in the back body part such that central tip portions of the curved portions therein project in a direction that becomes distant from the crotch portion.

2. The underpants type disposable diaper cover according to claim 1, wherein start and end points of at least one of the curved elastic members are positioned at the waist opening.

3. The underpants type disposable diaper cover according to claim 1, wherein the waist portion-elastic members are separated from the curved portions of the curved elastic members in each of the front and back body parts, and a plurality of waist elastic members are spaced in the longitudinal direction, reaching from one side to the other side along a waist, so as to pass through at least the separation area.

4. The underpants type disposable diaper cover according to claim 1, wherein the curved portion of at least one of the curved elastic members is configured in the front body part as to pass through an edge of the upper end portion of the attached absorbent pad.

* * * * *